United States Patent

Celliers et al.

Patent Number: 6,022,309
Date of Patent: Feb. 8, 2000

[54] OPTO-ACOUSTIC THROMBOLYSIS

[75] Inventors: Peter Celliers, Berkeley; Luiz Da Silva, Danville; Michael Glinsky, Livermore; Richard London, Orinda; Duncan Maitland, Livermore; Dennis Matthews, Moss Beach; Pat Fitch, Livermore, all of Calif.

[73] Assignee: The Regents of the University of California, Oakland, Calif.

[21] Appl. No.: 08/639,017

[22] Filed: Apr. 24, 1996

[51] Int. Cl.$^7$ .................................................. A61B 17/36
[52] U.S. Cl. .......................................................... 600/7
[58] Field of Search ............................... 606/2, 4, 7, 10, 606/11, 14–16

[56] References Cited

U.S. PATENT DOCUMENTS

| | | |
|---|---|---|
| 3,565,062 | 2/1971 | Kuris . |
| 3,858,577 | 1/1975 | Bass et al. . |

(List continued on next page.)

FOREIGN PATENT DOCUMENTS

| | | |
|---|---|---|
| 380634B | 11/1985 | Austria . |
| 0144764 | 6/1984 | European Pat. Off. . |
| 0194856 | 11/1986 | European Pat. Off. . |
| 0362466 | 12/1989 | European Pat. Off. . |
| 0454312 | 5/1991 | European Pat. Off. . |
| 0572435 | 1/1992 | European Pat. Off. . |
| 0707831 | 10/1995 | European Pat. Off. . |
| WO8606269 | of 1986 | WIPO . |
| WO9007904 | of 1990 | WIPO . |
| WO9206739 | of 1992 | WIPO . |
| WO9307806 | of 1993 | WIPO . |
| WO9314869 | of 1993 | WIPO . |
| WO9527587 | 10/1995 | WIPO . |

OTHER PUBLICATIONS

Prince et al., "Preferential Ablation of Calcified Arterial Plaque with Laser–Induced Plasmas", Journal of Quantum Electronics, vol. QE–23, No. 10, pp. 1783–1786, Oct. 1987.

Hayes et al., "Engineering of a Multifiber Catheter with an Optical Shield for Laser Angiosurgery", Proceedings of the Ninth Annual Conference of the IEEE Engineering in Medicine and Biology Society, vol. 1, pp. 200–202, Nov. 13–16, 1987.

Van Leeuwen et al., "Noncontact Tissue Ablation by Holmium: YSGG Laser Pulses in Blood", Lasers in Surgery and Medicine, vol. 11, pp. 26–34, 1991.

Scheu et al. "A New Concept for a Realtime Feedback System in Angioplasty with a Flashlamp Pumped Dye Laser", Lasers in Surgery and Medicine, vol. 11, No. 2, pp. 133–140, 1991.

de la Torre et al., "Cavitation Bubbles and Accoustic Transients May Produce Dissections During Laser Angioplasty", JACC, vol. 19, No. 3, pp. 48A, Mar. 1, 1992.

Zwaan et al., "Initial Clinical Experience with a new Pulsed Dye Laser Device in Angioplasty of Limb Ischemia and Shunt Fistula Obstructions", European Journal of Radiology, vol. 14, No. 1, pp. 72–76, 1992.

(List continued on next page.)

Primary Examiner—Samuel Gilbert

[57] ABSTRACT

This invention is a catheter-based device for generating an ultrasound excitation in biological tissue. Pulsed laser light is guided through an optical fiber to provide the energy for producing the acoustic vibrations. The optical energy is deposited in a water-based absorbing fluid, e.g. saline, thrombolytic agent, blood or thrombus, and generates an acoustic impulse in the fluid through thermoelastic and/or thermodynamic mechanisms. By pulsing the laser at a repetition rate (which may vary from 10 Hz to 100 kHz) an ultrasonic radiation field can be established locally in the medium. This method of producing ultrasonic vibrations can be used in vivo for the treatment of stroke-related conditions in humans, particularly for dissolving thrombus or treating vasospasm. The catheter can also incorporate thrombolytic drug treatments as an adjunct therapy and it can be operated in conjunction with ultrasonic detection equipment for imaging and feedback control and with optical sensors for characterization of thrombus type and consistency.

117 Claims, 5 Drawing Sheets

U.S. PATENT DOCUMENTS

| | | |
|---|---|---|
| 3,866,599 | 2/1975 | Johnson . |
| 3,884,236 | 5/1975 | Krasnov . |
| 4,204,528 | 5/1980 | Termanini . |
| 4,207,874 | 6/1980 | Choy . |
| 4,309,998 | 1/1982 | Aron nee Rosa et al. . |
| 4,418,688 | 12/1983 | Loeb . |
| 4,448,188 | 5/1984 | Loeb . |
| 4,587,972 | 5/1986 | Morantte, Jr. . |
| 4,641,650 | 2/1987 | Mok . |
| 4,686,979 | 8/1987 | Gruen et al. . |
| 4,716,288 | 12/1987 | Doi . |
| 4,770,653 | 9/1988 | Shturman .................................. 604/21 |
| 4,775,361 | 10/1988 | Jacques et al. ........................... 604/20 |
| 4,785,806 | 11/1988 | Deckelbaum . |
| 4,788,975 | 12/1988 | Shturman et al. . |
| 4,791,926 | 12/1988 | Fry . |
| 4,800,876 | 1/1989 | Fox et al. . |
| 4,813,930 | 3/1989 | Elliott ...................................... 604/53 |
| 4,862,886 | 9/1989 | Clarke et al. . |
| 4,867,141 | 9/1989 | Nakada et al. .............................. 601/4 |
| 4,887,600 | 12/1989 | Watson et al. . |
| 4,887,605 | 12/1989 | Angelsen et al. . |
| 4,932,954 | 6/1990 | Wondrazek et al. . |
| 4,939,336 | 7/1990 | Meyer et al. . |
| 5,005,180 | 4/1991 | Edelman et al. .......................... 372/57 |
| 5,026,366 | 6/1991 | Leckrone .................................... 606/7 |
| 5,026,367 | 6/1991 | Leckrone et al. ........................... 606/7 |
| 5,041,108 | 8/1991 | Fox et al. . |
| 5,041,121 | 8/1991 | Wondrazek et al. ...................... 606/15 |
| 5,058,570 | 10/1991 | Idemoto et al. .......................... 128/24 |
| 5,059,200 | 10/1991 | Tulip ...................................... 606/2.5 |
| 5,069,664 | 12/1991 | Guess et al. .............................. 604/22 |
| 5,109,859 | 5/1992 | Jenkins . |
| 5,116,227 | 5/1992 | Levy . |
| 5,158,560 | 10/1992 | Sogawa et al. .......................... 606/15 |
| 5,163,421 | 11/1992 | Bernstein et al. . |
| 5,188,632 | 2/1993 | Goldenberg ............................... 606/7 |
| 5,193,526 | 3/1993 | Daikuzono . |
| 5,197,470 | 3/1993 | Helfer et al. . |
| 5,224,942 | 7/1993 | Beuchat et al. . |
| 5,242,454 | 9/1993 | Gundlach et al. . |
| 5,246,447 | 9/1993 | Rosen et al. . |
| 5,254,112 | 10/1993 | Sinofsky et al. . |
| 5,254,114 | 10/1993 | Reed, Jr. et al. . |
| 5,269,778 | 12/1993 | Rink et al. . |
| 5,281,212 | 1/1994 | Savage et al. . |
| 5,304,115 | 4/1994 | Pflueger et al. .......................... 604/22 |
| 5,304,171 | 4/1994 | Gregory et al. .......................... 606/15 |
| 5,324,255 | 6/1994 | Passafaro et al. ......................... 604/22 |
| 5,326,342 | 7/1994 | Pflueger et al. .......................... 604/22 |
| 5,334,207 | 8/1994 | Gay, Jr. ...................................... 606/7 |
| 5,350,375 | 9/1994 | Deckelbaum et al. ....................... 606/7 |
| 5,354,324 | 10/1994 | Gregory .................................... 607/92 |
| 5,366,490 | 11/1994 | Edwards et al. .......................... 607/99 |
| 5,368,558 | 11/1994 | Nita .......................................... 604/22 |
| 5,370,609 | 12/1994 | Drasler et al. ............................ 604/22 |
| 5,377,683 | 1/1995 | Barken . |
| 5,380,273 | 1/1995 | Dubrul et al. ............................ 604/22 |
| 5,395,361 | 3/1995 | Fox et al. . |
| 5,397,293 | 3/1995 | Alliger et al. .............................. 601/2 |
| 5,397,301 | 3/1995 | Pflueger et al. .......................... 604/22 |
| 5,399,158 | 3/1995 | Lauer et al. .............................. 604/22 |
| 5,472,406 | 12/1995 | de la Torre et al. ........................ 601/2 |
| 5,473,136 | 12/1995 | Engelhardt et al. . |
| 5,486,170 | 1/1996 | Winston et al. . |
| 5,496,305 | 3/1996 | Kittrell et al. . |
| 5,496,306 | 3/1996 | Engelhardt et al. . |
| 5,571,151 | 11/1996 | Gregory . |
| 5,586,981 | 12/1996 | Hu . |
| 5,662,590 | 9/1997 | de la Torre et al. . |

OTHER PUBLICATIONS

Fair, Jr., "In Vitro Destruction of Urinary Calculi by Laser–Induced Stress Waves", Medical Instrumentation, vol. 12, No. 2, Mar.–Apr. 1978, pp. 100–105, Assn. for the Advancement of Medical Instrumentation.

Fujii et al., "Multispot Laser Photocoagulation System Using a Fiber Bundle Scanner", Applied Optics, vol. 21, No. 19, pp. 3437–3442, Oct. 1, 1982, New York.

Lee et al., "Feasibility of Intravascular Laser Irradiation for in vivo Visualization and Therapy of Cardiocirculatory Diseases", American Heart Journal, Jun. 1982, pp. 1076–1077.

Abela et al., "Effects of Carbon Dioxide, Nd–YAG, and Argon Laser Radiation on Coronary Atheromatous Plaques", The American Journal of Cardiology, vol. 50, No. 6, pp. 1199–1205, Dec. 1982.

Choy et al., "Laser Coronary Angioplasty: Experience with 9 Cadaver Hearts", 3 pps., from the Lenox Hill Hospital Laser and Cardiac Catherterization Laboratories, New York NY; manuscript accepted Jun. 1982.

Choy et al., "Transluminal Laser Catheter Angioplasty", 3 pps., from the Lenox Hill Hospital, New York, NY, manuscript accepted Jul. 1992.

Anderson et al., "Selective Photothermolysis: Precise Microsurgery by Selective Absorption of Pulsed Radiation", Science, vol. 220, pp. 524–527, Apr. 1983.

Gillen et al., "Recanalization of Arteries by Laser Radiation", Journal of Medical Engineering and Technology, No. 21, pp. 215–217, 1984.

Kaminow et al., "Argon Laser Disintegration of Thrombus and Atherosclerotic Plaque", Applied Optics, vol. 23, No. 9, pp. 1301–1302, May 1, 1984.

Choy et al., "Human Coronary Laser Recanalization", Clinical Cardiology, vol. 7, pp. 377–381, accepted Apr. 1984.

Muller et al., "Excimer Lasers Offer Promise in Surgical Applications", Laser Focus/Electro–Optics, Jul. 1985, pp. 72–81.

German article (English translation attached): Schmidt–Kloiber, Aktuelle Nephrologie, Heft. 1, 1978, Wissenschaftliche Informationen, Fresenius–Stiftung, pp. 116–148.

Deckelbaum et al., "Reduction of Laser–Induced Pathologic Tissue Injury Using Pulsed Energy Delivery", The American Journal of Cardiology, Oct. 1, 1985, vol. 56, pp. 662–666.

Sathyam et al., "Visualization of Microsecond Laser Ablation of Porcine Clot and Gelatin Under a Clear Liquid," pp. 28–35, Proceedings of Lasers in Surgery: Advanced Characterization, Therapeutics, & Systems VI, Jan. 27–30, 1996.

Jansen et al., Effect of Pulse Duration on Bubble Formation and Laser–Induced Pressure Waves During Holmium Laser Ablation, Lasers in Surgery and Medicine, vol. 18, pp. 278–293 (1996).

Fujimoto et al., "Time–Resolved Studies of Nd: YAG Laser–Induced Breakdown", Investigative Ophthalmology & Visual Science, Dec. 1985, pp. 1771–1777.

Vogel et al., "Cavitation Buble Dynamics and Acoustic Transient Generation in Ocular Surgery with Pulsed Neodymium: YAG Lasers", Ophthalmology, vol. 93, No. 10, pp. 1259–1268, Oct. 1986.

Kittrell et al., "Multifiber Optically–Shielded Catheter for Laser Angiosurgery", Optical Fibers in Medicine II, vol. 713, pp. 58–63, Sep. 17–19 1986.

van Leeuwen et al., "Bubble Formation during Pulsed Laser Ablation: Mechanism and Implications", Progress in Biomedical Optics, vol. 1882, pp. 13–21, 1993.

Pettit et al., "Thrombolysis by Excimer Laser Photoablation", Lasers in Life Sciences, vol. 5, No. 3, pp. 185–197, 1993.

Chapyak et al., "Numerical Studies of Bubble Dynamics in Laser Thrombolysis", Progress in Biomedical Optics, vol. 2671, pp. 84–87, 1996.

Shangguan et al., "Investigation of Cavitation Bubble Dynamics Using Particle Image Velocimetry: Implications for Photoacoustic Drug Delivery", Progress in Biomedical Optics, vol. 2671, pp. 104–115, 1996.

Nighan, Jr. et al., "DPSS Lasers Challenge Water–Cooled Ion Lasers", Laser Focus World, vol. 32, No. 4, pp. 63–70, 1996.

OPTO-ACOUSTIC THROMBOLYSIS

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention is directed to the removal of blockages in tubular tissues and organs, and more specifically, it relates to the removal of intravascular occlusions such as atherosclerotic plaque or thrombus.

2. Description of Related Art

Ischemic strokes are caused by the formation or lodging of thrombus in the arterial network supplying the brain. Typically these occlusions are found in the carotid artery or even smaller vessels located still higher in the cranial cavity. Interventional cardiologists and vascular surgeons have devised minimally invasive procedures for treating these conditions in the vasculature elsewhere in the body. Among these treatments is ultrasound angioplasty whereby a micro, catheter is directed to the site of an occlusion. An ultrasonic transducer is coupled to a transmission medium that passes within the catheter and transmits vibrations to a working tip at the distal end in close proximity to the occlusion. Ultrasonic catheters for dissolving atherosclerotic plaque and for facilitating clot lysis have been described previously. Improvements on these inventions have concentrated on improving the operation or function of the same basic device (Pflueger et al., U.S. Pat. No. 5,397,301). The vibrations coupled into the tissues help to dissolve or emulsify the clot through various ultrasonic mechanisms such as cavitation bubbles and microjets which expose the clot to strong localized shear and tensile stresses. These prior art devices are usually operated in conjunction with a thrombolytic drug and/or a radiographic contrast agent to facilitate visualization.

The ultrasonic catheter devices all have a common configuration in which the source of the vibrations (the transducer) is external to the catheter. The vibrational energy is coupled into the proximal end of the catheter and transmitted down the length of the catheter through a wire that can transmit the sound waves. There are associated disadvantages with this configuration: loss of energy through bends and curves with concomitant heating of the tissues in proximity; the devices are not small enough to be used for treatment of stroke and are difficult to scale to smaller sizes; it is difficult to assess or control dosimetry because of the unknown and varying coupling efficiency between the ultrasound generator and the distal end of the catheter. Dubrul et al., U.S. Pat. No. 5,380,273, attempts to improve on the prior art devices by incorporating advanced materials into the transmission member. Placement of the ultrasonic transducer itself at the distal end of the catheter has been impractical for a number of reasons including size constraints and power requirements.

A related method for removing occlusions is laser angioplasty in which laser light is directed down an optical fiber to impinge directly on the occluding material. Laser angioplasty devices have been found to cause damage or destruction of the surrounding tissues. In some cases uncontrolled heating has lead to vessel perforation. The use of high energy laser pulses at a low or moderate repetition rate, e.g. around 1 Hz to 100 Hz, results in nondiscriminatory stress waves that significantly damage healthy tissue and/or insufficient target-tissue removal when the independent laser parameters are adjusted such that healthy tissue is not affected. Use of high energy laser light to avoid thermal heating has been found to cause damage through other mechanisms associated with large cavitation bubbles and shock waves that puncture or otherwise adversely affect the tissue.

SUMMARY OF THE INVENTION

It is an object of the present invention to provide means for dissolution of a vascular occlusion with a high frequency train of low energy laser pulses which generate ultrasonic excitation in the fluids in close proximity to the occlusion.

Energy transmission through a catheter is provided by using an optical fiber to guide laser pulses to the distal end. However, unlike laser angioplasty or laser thrombolysis, the present invention does not rely on direct ablation of the occlusion, but instead uses a high frequency train of low energy laser pulses to generate ultrasonic excitations in the fluids in close proximity to the occlusion. Dissolution of the occlusion is then prompted by ultrasonic action and/or by emulsification, and not directly by the interaction with the laser light. The key to inducing an ultrasonic response in the tissues and fluids lies in careful control of the wavelength, pulse duration, pulse energy and repetition rate of the laser light. The use of optical energy to induce an ultrasonic excitation in the tissue offers a number of advantages. Optical fibers can be fabricated to small dimensions, yet are highly transparent and capable of delivering substantial optical power densities from the source to the delivery site with little or no attenuation. Optical fibers are also flexible enough to navigate all vessels of interest. The present invention allows delivery of sufficient energy to generate the acoustic excitation through a small and flexible catheter, such as is required for stroke treatment. The method may also incorporate a feedback mechanism for monitoring and controlling the magnitude of the acoustic vibrations induced in the tissue.

DETAILED DESCRIPTION OF THE INVENTION

The invention incorporates a catheter containing an optical fiber. The optical fiber is coupled at the proximal end to a high repetition rate laser system which injects pulses of light into the fiber. The light emerging from the fiber at the distal end is absorbed by the fluid surrounding the catheter. This fluid may be blood, a biological saline solution containing an absorbing dye, a thrombolytic pharmaceutical or thrombus itself The optical fiber functions as a means of energy transmission such that the optical energy produced by the laser is delivered to the end of the fiber. The laser light emerging from the distal end of the fiber optic has a pulse frequency within the range of 10 Hz to 100 kHz, a wavelength within the range of 200 nm to 5000 nm and an energy density within the range of 0.01 J/cm$^2$ to 4 J/cm$^2$. In one embodiment, the pulse frequency is within the range of 5 kHz to 25 kHz.

Figure 1A:
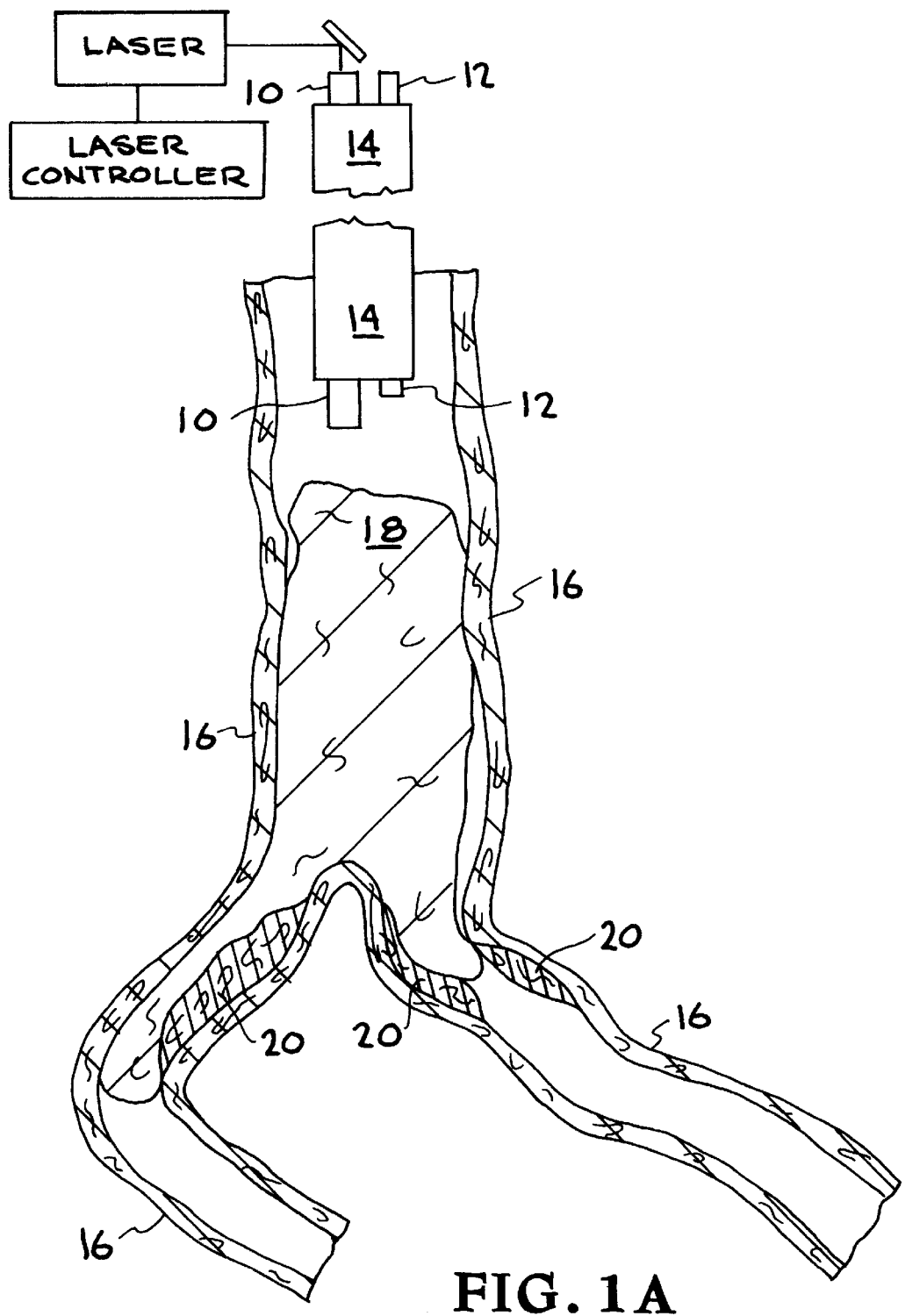
FIG. 1A shows a sketch of an application of the optical fiber-based opto-acoustic thrombolysis catheter of the present invention.
Figure 1B:
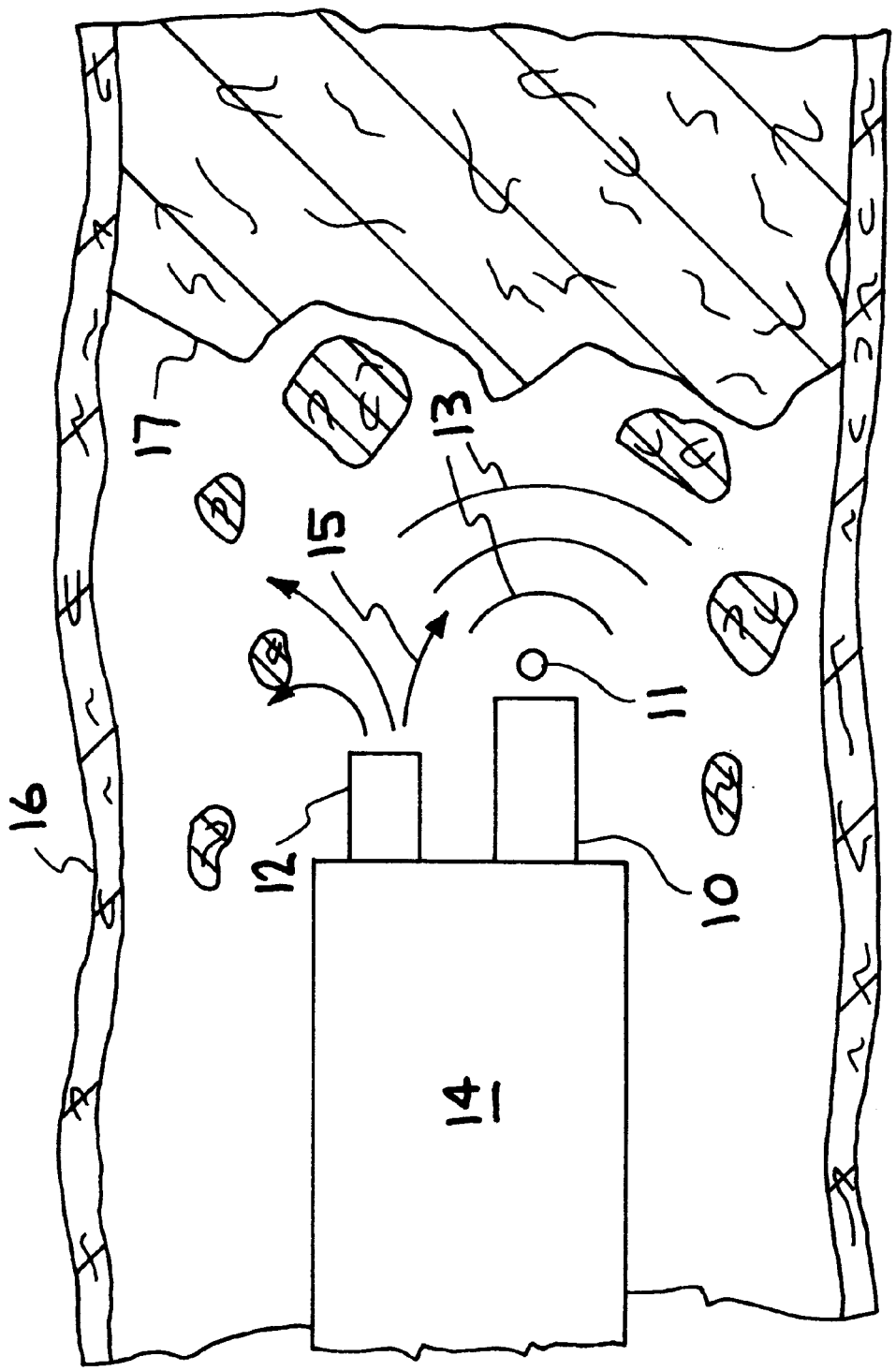
FIG. 1B depicts the ultrasonic dissolution of a blockage using an adjunct fluid.

Lysis of thrombus, atherosclerotic plaque or any other occluding material in the tubular tissue is facilitated by an ultrasonic radiation field created in the fluids near the occlusion. As an adjunct treatment, a working channel which surrounds or runs parallel to the optical fiber may be used to dispense small quantities of thrombolytic drugs to facilitate further lysis of any significantly sized debris (>5 μm dia. particles) left over from the acoustic thrombolysis process. The conversion of optical to acoustic energy may proceed through several mechanisms that may be thermoelastic, thermodynamic or a combination of these. FIG. 1A shows an optical fiber 10 with a parallel working channel 12, where both the fiber 10 and the working channel 12 are both located within a catheter 14 which has been inserted into a blood vessel 16. The distal end of fiber 10 is placed near thrombus 18 and stenotic plaque 20 within blood vessel 16. A laser 2, controlled by laser controller 4, provides laser light 6 into fiber 10. In FIG. 1B, fiber 10 delivers laser light to produce a collapsing cavitation bubble 11 and the resulting expanding acoustic wave 13. A parallel working channel 12 in catheter 14 delivers an adjunct fluid 15 to aid in the removal of occlusion 17 from inside blood vessel 16.

Figure 2A:
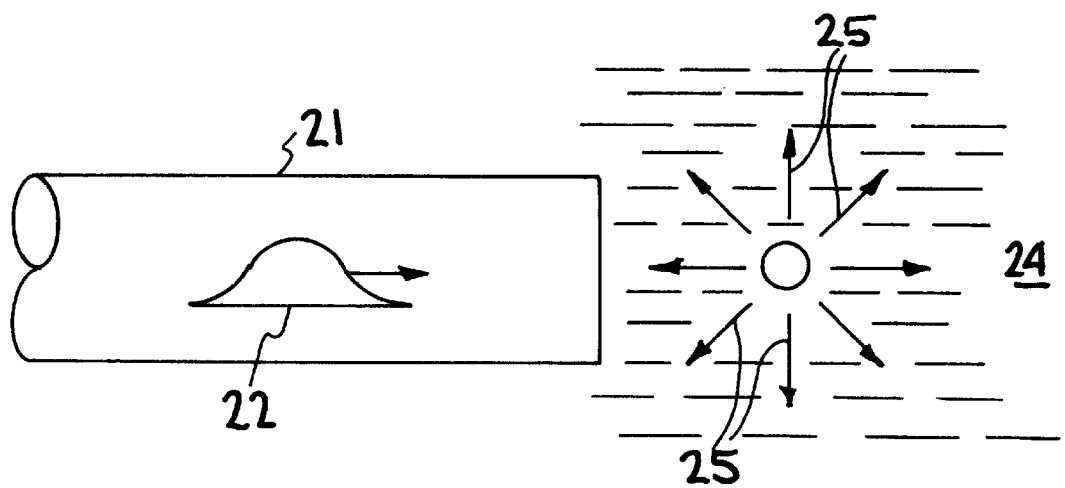
FIGS. 2A–C depict the thermo-elastic operation of the present invention.
Figure 2B:
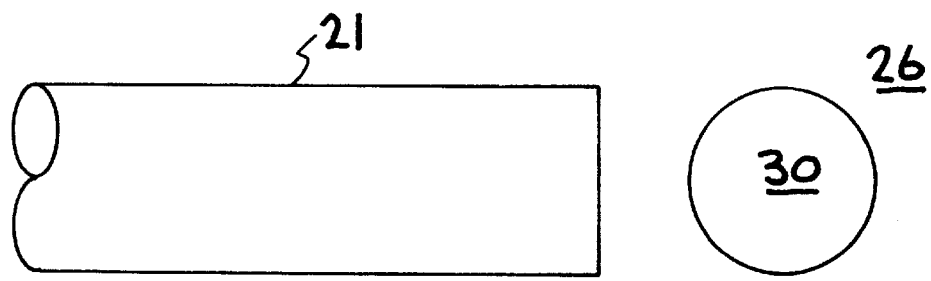
Figure 2C:
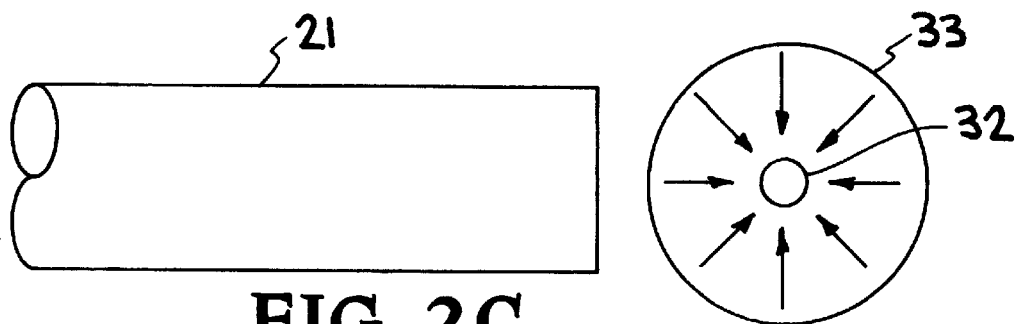

As depicted in FIGS. 2A–C, in the thermoelastic mode, each laser pulse 22 delivers a controlled level of energy in the fluid 24 which creates a large thermoelastic stress in a small volume of the fluid. The expanding direction of this stress is indicated by arrows 25 in FIG. 2A. The volume of fluid 24 which is heated by the laser pulse 22 is determined by the absorption depth of the laser light in the fluid 24, and must be controlled to produce a desired size. For example, an appropriate size may be the fiber diameter, or a distance comparable to some fraction of the vessel containing the occlusion. This can be adjusted by controlling the laser wavelength or the composition of the fluid such that most of the laser energy is deposited in a fluid depth of the desired size. The laser pulse duration is short enough to deposit all of the laser energy into the absorbing fluid in a time scale shorter than the acoustic transit time across the smallest dimension of absorbing region. This is an isochoric (constant volume) heating process. For an absorption volume of approximately 100 μm in diameter the acoustic transit time is approximately 70 ns, so the deposition time must be significantly less than this, e.g., around 10 ns.

The absorbing fluid responds thermoelasticaly to the deposition of energy such that a region of high pressure is created in the fluid in the heated volume. The boundary of the high pressure zone decays into a pattern of acoustic waves: a compression wave propagates away from the energy deposition region (diverging wave front) and a rarefaction wave propagates towards the center of the energy deposition region (converging wave front). When the rarefaction wave converges on the center of the initial deposition region, it creates a region 26 of tensile stress that promotes the formation of a cloud of cavitation bubbles which coalesce to form a larger bubble 30. Eventually, the cavitation bubble collapses (32), resulting in an expanding acoustic wave 33. Collapse and subsequent rebound of the cavitation bubble will generate acoustic impulses in the surrounding fluid, which will carry off a portion of the energy of the cavity. The collapse and rebound processes take place on a time scale governed principally by the fluid density and the maximum size of the initial cavity. The first collapse and rebound will be followed by subsequent collapse and rebound events of diminishing intensity until the energy of the cavity is dissipated in the fluid. Subsequent laser pulses are delivered to repeat or continue this cycle and generate an ultrasonic radiation field at a frequency or frequencies determined by the laser pulse frequency.

To summarize, a device operating through the first mode produces an ultrasonic radiation field in the fluid by: (i) depositing laser energy in a volume of fluid comparable to the fiber dimension in a time scale of duration less than the acoustic transit time across this dimension (as controlled by choice of laser wavelength and absorbing fluid as the case may be); (ii) controlling the laser energy such that the maximum size of the cavitation bubble is approximately the same as the fiber diameter; and (iii) pulsing the laser at a repetition rate such that multiple cycles of this process generate an acoustic radiation field in the surrounding fluid; resonant operation may be achieved by synchronizing the laser pulse repetition rate with the cavity lifetime. Typical operation leads to a fluid-based transducer that cycles at 1–100 kHz with a reciprocating displacement of 100–200 μm (for typical optical fiber dimensions). This displacement is very similar to that found in mechanically-activated ultrasound angioplasty devices.

Figure 3A:
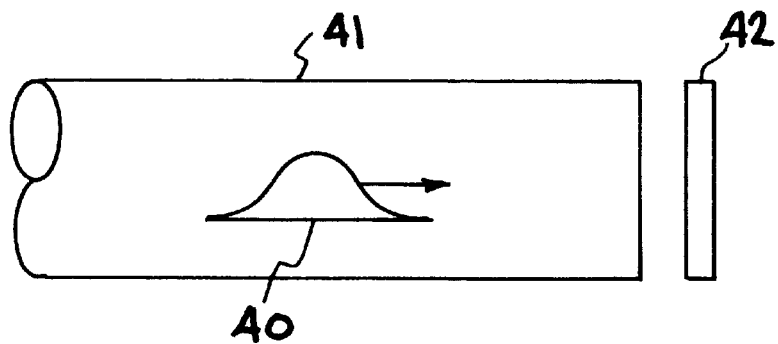
FIGS. 3A–C depict the superheated vapor expansion mode of the present invention.
Figure 3B:
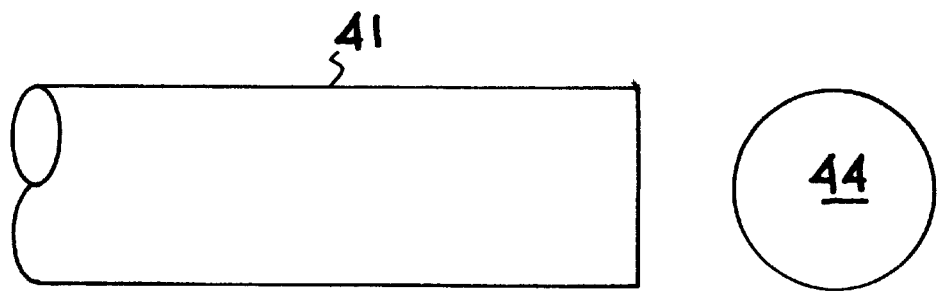
Figure 3C:
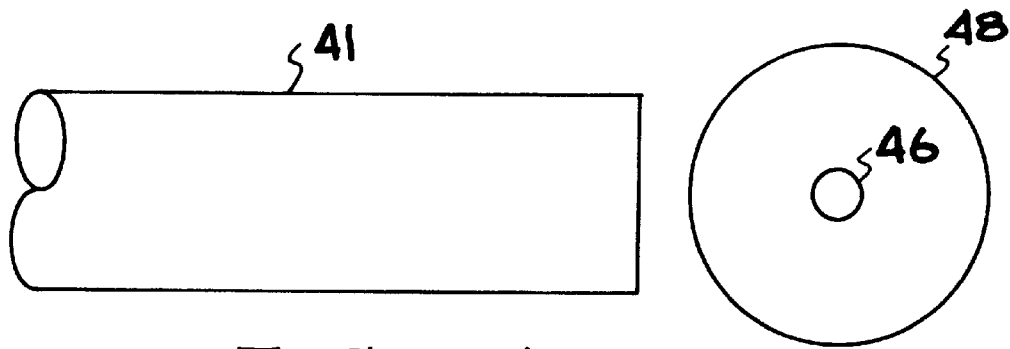

In the superheated vapor expansion mode, as shown in FIGS. 3A–C, in fiber optic 41, each laser pulse 40 delivers a controlled level of energy in the fluid within an absorption depth which is very small compared to the characteristic size of the vessel containing the catheter, or even small compared to the fiber diameter. The absorption depth may also be small compared to the distance that a sound wave travels in the duration of the laser pulse. The laser energy deposits a sufficient level of energy to heat all of the fluid within the absorption depth well above the vaporization temperature of the fluid at the ambient pressure. In the process of depositing the laser energy, a thermoelastically-generated acoustic wave is launched in the fluid, which propagates out from the heated region. On time scales longer than 1 μs, the superheated fluid 42 undergoes vaporization, which creates a bubble of vapor. As the fluid vaporizes, its volume 44 increases by a large factor, hence the need for involving only a small layer of fluid such that the ultimate size of the vapor bubble does not exceed, for example, the vessel diameter.

The laser pulse duration need not be restricted to times as short as in the thermoelastic mode since the bubble expansion is nearly an isobaric process; however, the laser pulse duration should be shorter than the bubble expansion time, and it should be much shorter than a typical thermal relaxation time for the superheated region. (According to the Rayleigh bubble collapse theory the bubble lifetime is approximately 25 μs for a 50 μm diameter bubble; thermal relaxation occurs on a few hundred microsecond time scale, so the laser pulse should be several microseconds or less in duration). The vapor bubble expands up to a maximum radius which depends on the vapor pressure initially created in the fluid. At the maximum bubble radius, the vapor pressure in the expanded bubble has dropped to well below the ambient pressure and the bubble 46 undergoes collapse, resulting in an expanding acoustic wave 48. Rebound and subsequent collapse events may take place following the first collapse. The bubble expansion and collapse couples acoustic energy into the fluid. Subsequent laser pulses are delivered to repeat or continue this cycle and generate an ultrasonic radiation field at a frequency or frequencies determined by the laser pulse frequency. Similar to the first mode, a resonant operation may be achieved by matching the laser pulse period to the lifetime of the vapor bubble.

To summarize, a device operating through the second mode produces an ultrasonic radiation field in the fluid by: (i) depositing laser energy in a small volume of fluid (as controlled by choice of laser wavelength and absorbing fluid as the case may be); (ii) controlling the laser energy such that the maximum size of the vapor bubble is approximately the same as or less than the diameter of the vessel being treated; and (iii) pulsing the laser energy at a repetition rate such that multiple cycles of the bubble generation and collapse process generates an acoustic radiation field in the surrounding fluid. Unlike the first mode, the delivery time is not a significant issue, so longer pulse duration lasers (up to several $\mu s$) may be useful.

For either mode of operation the laser wavelength, laser pulse duration and laser absorption depth must be precisely, controlled such that an adequate acoustic response is obtained with a minimum of laser pulse energy. For the first mode this entails matching the absorption volume to a characteristic dimension of the system such as the fiber diameter or some fraction of the vessel diameter, and using a short laser pulse (less than 20 ns). For second mode this entails depositing the laser energy in a very small absorption depth to achieve a sufficient level of superheat in a small fluid mass such as can be accommodated by a small energy budget and without creating a vapor bubble so large as to be damaging to the surrounding tissues.

These opto-acoustic modes of coupling laser energy into acoustic excitations in tissues include a number of features. Low to moderate laser pulse energy combined with high repetition rate avoids excessive tissue heating or intense shock generation. Localized absorption of the laser energy occurs. Laser energy may interact thermoelastically or thermodynamically with the ambient fluids. An acoustic radiation field is generated by repeated expansion and collapse of a bubble at the tip of the fiber. Resonant operation may be achieved by matching the laser pulse period to the lifetime of the generated bubble. Soft fibrous occlusions (thrombus) may be dissolved by generating the bubbles directly within the thrombus.

Figure 4A:
FIG. 4A shows a fiber optic having a concave tip.
Figure 4B:
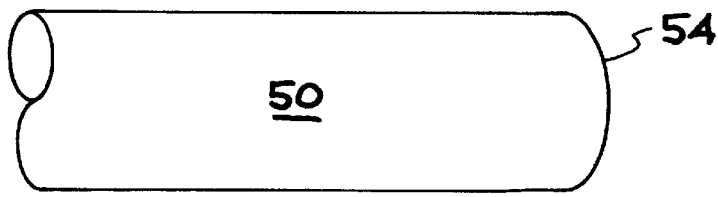
FIG. 4B shows a fiber optic having a convex tip.
Figure 5:
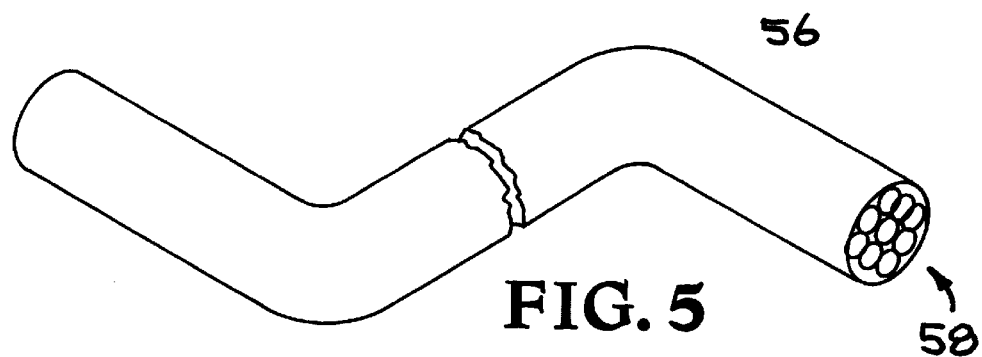
FIG. 5 shows a bundle of fiber strands.

Control and/or manipulation of the spatial and temporal distribution of energy deposited in the fluid at the fiber tip can be used modify the near field acoustic radiation pattern, for example, to concentrate acoustic energy on an object in proximity to the fiber, or to distribute the acoustic radiation more uniformly. Techniques based on this strategy will be most successful for a special case of thermoelastic response (first mode) where the laser pulse duration is short and the fluid absorption is also relatively strong, such that the laser energy is deposited in a thin layer adjacent to the surface of the fiber tip. For example, by forming a concave surface on the fiber tip, the optical energy is deposited in the fluid in a similar shaped distribution. Acoustic waves emitted from this concave distribution will tend to focus to a point at a distance R from the fiber tip, where R is the radius of curvature of the concave surface. A planar fiber tip will generate an initially planar acoustic wavefront in proximity the fiber tip. A convex fiber tip will produce a diverging spherical wavefront which will disperse the acoustic energy over a larger solid angle. Another means of modifying the near field radiation pattern may be to use a fiber bundle through which the laser energy is delivered, and control the temporal distribution of deposited laser energy. The laser energy may be arranged to arrive at individual fiber strands in the catheter tip at different times, which, in combination with the different spatial positions of these individual strands, can be adjusted to control the directionality and shape of the acoustic radiation pattern, similar to phased-array techniques used in radar. FIG. 4A shows a modified fiber optic 50 having a concave distal end 52. FIG. 4B shows a fiber optic 50 with a convex distal end 54. FIG. 5 shows a modified fiber optic 56 consisting of a bundle of fiber strands 58, through each of which laser pulse energy is delivered at varying times.

Figure 6:
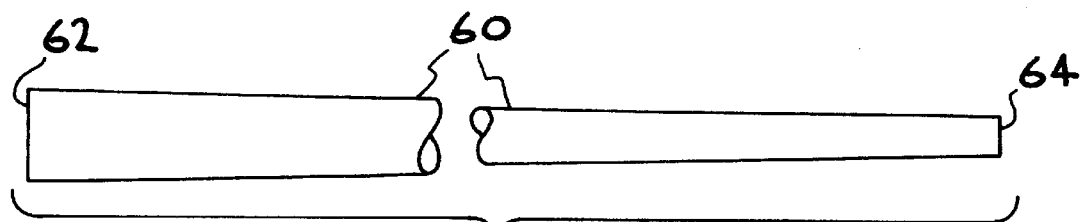
FIG. 6 shows a variable diameter fiber optic.

Commercial fibers are usually jacketed to protect them from the environment. "Bare" or unjacketed fibers are available. It is helpful to use coatings on fibers to make them slide more easily through catheters. As shown in FIG. 6, a variable diameter optical fiber 60 allows for greater physical strength at the proximal end 62 and greater access at the distal end 64. This can be accomplished through modifying existing fibers (stripping the protective sheath from around the core) or by making custom fibers. Custom fabrication can be accomplished by varying the extrusion or draw rate for the fiber. Glass or plastic composition can be changed as a function of drawing the fiber so that greater control of the fiber from a distal end is achieved without sacrificing optical quality. One particular instance of this is to treat the tip so that it is "soft," so the end will not jam in the catheter sheath. Also, shape memory in the tip allows steering of the fiber when it protrudes from the distal end of the catheter sheath.

Figure 7:
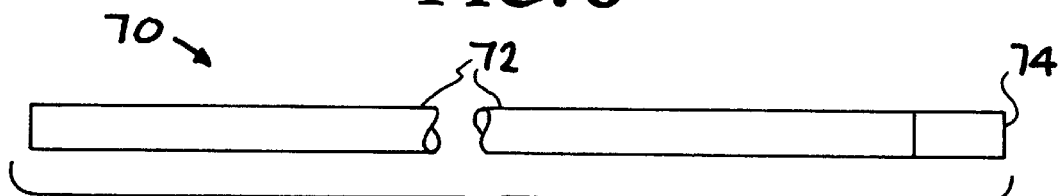
FIG. 7 shows a composite of a glass/plastic fiber.

FIG. 7 shows a composite of a glass/plastic fiber. Fiber 70 comprises a glass portion 72 with a relatively short plastic tip 74 which has a length within the range of a millimeter to a several centimeters. Due to the rigidity of the glass portion 72, a fiber optic having this configuration is easily pushed through vasculature. The softer plastic tip 74 is less likely to puncture a vein wall than a glass tip. This configuration could include an additional glass tip to increase the durability of the fiber optic.

Acoustic energy at many frequencies is generated in the present invention, and may be considered as a signal source for producing acoustic images of structures in body tissues. Any signal detection and analysis system which relies on a point source of acoustic radiation to produce the signal may be used with this invention.

Applications envisioned for this invention include any method or procedure whereby localized ultrasonic excitations are to be produced in the body's tissues through application of a catheter. The invention may be used in (i) endovascular treatment of vascular occlusions that lead to ischemic stroke (This technology can lyse thrombus and lead to reperfusion of the affected cerebral tissue), (ii) endovascular treatment of cerebral vasospasm (This technology can relax vaso-constriction leading to restoration of normal perfusion and therefore prevent further transient ischemic attacks or other abnormal perfusion situations), (iii) endovascular treatment of cardiovascular occlusions (This technology can lyse thrombus or remove atherosclerotic plaque from arteries), (iv) endovascular treatment of stenoses of the carotid arteries, (v) endovascular treatment of stenoses of peripheral arteries, (vi) general restoration of patency in any of the body's luminal passageways wherein access can be facilitated via percutaneous insertion, (vii) any ultrasonic imaging application where a localized (point) source of ultrasonic excitation is needed within an organ or tissue location accessible through insertion of a catheter, (viii) lithotriptic applications including therapeutic removal of gallstones, kidney stones or other calcified objects in the body and (ix) as a source of ultrasound in ultrasound modulated optical tomography.

The pulsed laser energy source used by this invention can be based on a gaseous, liquid or solid state medium. Rare earth-doped solid state lasers, ruby lasers, alexandrite lasers, Nd:YAG lasers and Ho:YLF lasers are all examples of lasers that can be operated in a pulsed mode at high repetition rate and used in the present invention. Any of these solid state lasers may incorporate non-linear frequency-doubling or frequency-tripling crystals to produce harmonics of the fundamental lasing wavelength. A solid state laser producing a coherent beam of ultraviolet radiation may be employed directly with the invention or used in conjunction with a dye laser to produce an output beam which is tunable over a wide portion of the ultraviolet and visible spectrum. Tunability over a wide spectrum provides a broad range of flexibility for matching the laser wavelength to the absorption characteristics of the fluids located at the distal end of the catheter. The output beam is coupled by an optical fiber to the surgical site through, for example, a percutaneous catheter. In operation, a pulsed beam of light drives the ultrasonic excitation which removes and/or emulsifies thrombus or atherosclerotic plaque with less damage to the underlying tissue and less chance of perforating the blood vessel wall than prior art devices.

Various other pulsed lasers can be substituted for the disclosed laser sources. Similarly, various dye materials and configurations can be used in the dye laser. Configurations other than a free-flowing dye, such as dye-impregnated plastic films or cuvette-encased dyes, can be substituted in the dye laser. The dye laser can also store a plurality of different dyes and substitute one for another automatically in response to user-initiated control signals or conditions encountered during use (e.g. when switching from a blood-filled field to a saline field or in response to calcific deposits). Suitable dyes for use in the dye laser components of the invention include, for example, P-terphenyl (peak wavelength 339); BiBuQ (peak wavelength: 385); DPS (peak wavelength: 405); and Coumarin 2 (peak wavelength: 448).

In yet another embodiment the pulsed light source may be an optical parametric oscillator (OPO) pumped by a frequency-doubled or frequency-tripled solid-state laser. OPO systems allow for a wide range of wavelength tunability in a compact system comprised entirely of solid state optical elements. The laser wavelength in OPO systems may also be varied automatically in response to user-initiated control signals or conditions encountered during use.

Catheters, useful in practicing the present invention, can take various forms. For example, one embodiment can consist of a catheter having an outer diameter of 3.5 millimeters or less, preferably 2.5 millimeters or less. Disposed within the catheter is the optical fiber which can be a 400 micron diameter or smaller silica (fused quartz) fiber such as the model SG 800 fiber manufactured by Spectran, Inc. of Sturbridge, Mass. The catheter may be multi-lumen to provide flushing and suction ports. In one embodiment the catheter tip can be constructed of radio-opaque and heat resistant material. The radio-opaque tip can be used to locate the catheter under fluoroscopy.

The invention can be used with various catheter devices, including devices which operate under fluoroscopic guidance as well as devices which incorporate imaging systems, such as echographic or photoacoustic imaging systems or optical viewing systems. For one example of a photoacoustic imaging system which can be specifically adapted for the catheter environment, see U.S. Pat. No. 4,504,727 incorporated herein by reference.

Changes and modifications in the specifically described embodiments can be carried out without departing from the scope of the invention, which is intended to be limited by the scope of the appended claims.

We claim:

1. A method for delivering acoustic energy into the cerebrovasculature during percutaneous transluminal access procedures, comprising:

inserting a fiber optic into the vasculature to a point near an occlusion, wherein said fiber optic comprises a proximal end and a distal end; and coupling laser light into said proximal end, wherein said laser light has (i) a pulse frequency within the range of 5 kHz to 25 kHz, (ii) a wavelength within the range of 200 nm to 5000 nm and (iii) an energy density within the range of 0.01 $J/cm^2$ to 4 $J/cm^2$, wherein said laser light emerges from said distal end and generates an acoustic radiation field in a liquid ambient medium, wherein said acoustic radiation field is generated through one or more mechanisms selected from a group consisting of thermoelastic expansion within said liquid ambient medium and superheated vapor expansion within said liquid ambient medium.

2. A method, comprising:

inserting a fiber optic into the vasculature to a point near an occlusion, wherein said fiber optic comprises a proximal end and a distal end; and coupling laser light into said proximal end, wherein said laser light has (i) a pulse frequency within the range of 10 Hz to 100 kHz, (ii) a wavelength within the range of 200 nm to 5000 nm and (iii) an energy density within the range of 0.01 $J/cm^2$ to 4 $J/cm^2$, wherein said laser light emerges from said distal end and generates an acoustic radiation field in a liquid ambient medium.

3. The method of claim 2, wherein said pulse frequency range comprises from about 1 kHz to 25 kHz.

4. The method of claim 3, wherein said laser light has a pulse duration of less than 200 ns, wherein said acoustic radiation field is generated through thermoelastic expansion of said liquid ambient medium.

5. The method of claim 3, wherein said acoustic radiation field is generated through superheated vapor expansion.

6. The method of claim 3, further comprising the step of removing said occlusion by applying said acoustic radiation field to said occlusion.

7. The method of claim 6, wherein said occlusion is selected from a group consisting of atherosclerotic plaque and thrombus.

8. The method of claim 3, further comprising the step of injecting said liquid ambient medium into the vasculature wherein said liquid ambient medium is selected from a group consisting of blood, a biological saline solution, a biological saline solution containing an absorbing dye, and a thrombolytic pharmaceutical.

9. The method of claim 3, wherein said fiber optic is located within a catheter, said method further comprising injecting through said catheter into said liquid ambient medium a thrombolytic drug to emulsify said occlusion.

10. The method of claim 9, wherein a working channel runs parallel to said fiber optic within said catheter, wherein the step of injecting through said catheter into said liquid ambient medium a thrombolytic drug to emulsify said occlusion includes injecting said thrombolytic drug through said working channel.

11. The method of claim 3, wherein said step of inserting a fiber optic into the vasculature includes inserting a fiber optic having a tip selected from a group consisting of a concave tip, and a planar tip.

12. The method of claim 3, wherein said step of inserting a fiber optic into the vasculature includes inserting a fiber optic having a variable diameter into said vasculature.

13. The method of claim 3, wherein said step of inserting a fiber optic into the vasculature includes inserting a fiber optic comprising a composite of glass and plastic into said vasculature.

14. The method of claim 3, wherein said acoustic radiation field is generated through a mechanism selected from a group consisting of thermoelastic, thermodynamic and a combination of thermoelastic and thermodynamic mechanisms, to remove said occlusion.

15. The method of claim 3, wherein said acoustic radiation field is generated to remove said occlusion, wherein said laser light has a pulse duration of less than 200 ns, wherein said acoustic radiation field is generated through thermoelastic expansion of said liquid ambient medium, wherein said laser light provides a controlled level of energy in said liquid ambient medium which creates a large thermoelastic stress in a small volume of said liquid ambient medium, wherein said volume of said liquid ambient medium that is heated by said laser light is determined by the absorption depth of said laser light in said liquid ambient medium, and wherein said absorption depth is controlled to produce a desired thermoelastic stress in said volume.

16. The method of claim 3, wherein said acoustic radiation field is generated to remove said occlusion, wherein said laser light has a pulse duration that is short enough to deposit substantially all of the laser energy into the absorbing fluid in a time scale shorter than the acoustic transit time across the smallest dimension of absorbing region, wherein said acoustic radiation field is generated through thermoelastic expansion of said liquid ambient medium.

17. The method of claim 3, wherein said liquid ambient medium is selected from a group consisting of blood, a biological saline solution, a biological saline solution containing an absorbing dye, a thrombolytic pharmaceutical, and thrombus.

18. The method of claim 3, wherein said fiber optic is located within a catheter, said method further comprising injecting through said catheter into said liquid ambient medium a radiographic contrast agent to facilitate visualization.

19. The method of claim 3, wherein said fiber optic comprises a bundle of fiber strands, each strand having a proximal and a distal end, wherein said coupling laser light into said proximal end comprises coupling said laser light into said strand proximal ends at varying times, wherein said laser light within individual strands of said bundle arrives at said strand distal ends at different times, wherein said different times are adjusted to control the directionality and shape of said acoustic radiation field, wherein said different times are adjusted in combination with the different spatial positions of said individual strands.

20. The method of claim 3, wherein said laser light has a pulse duration of less than 200 ns.

21. A method, comprising:
inserting a fiber optic into the vasculature to a point near an occlusion, wherein said fiber optic is located within a catheter, wherein said fiber optic comprises a proximal end and a distal end;
coupling laser light into said proximal end, wherein said laser light has (i) a pulse frequency within the range of from about 1 kHz to 25 kHz and (ii) a wavelength within the range of 200 nm to 5000 nm, wherein said laser light emerges from said distal end and generates an acoustic radiation field in a liquid ambient medium; and
injecting through said catheter into said liquid ambient medium a radiographic contrast agent to facilitate visualization.

22. A method, comprising:
inserting a fiber optic into the vasculature to a point near an occlusion, wherein said fiber optic comprises a proximal end and a distal end;
coupling laser light into said proximal end, wherein said laser light has (i) a pulse frequency within the range of from about 1 kHz to 25 kHz and (ii) a wavelength within the range of 200 nm to 5000 nm, wherein said laser light emerges from said distal end and generates an acoustic radiation field in a liquid ambient medium; and
monitoring and controlling the magnitude of the acoustic radiation field induced in the liquid ambient medium through a feedback mechanism.

23. A method, comprising:
inserting a bundle of fiber optic strands into the vasculature to a point near an occlusion, wherein each of said fiber optic strands comprises a proximal end and a distal end; and
coupling laser light into each of said proximal ends, wherein said laser light has (i) a pulse frequency within the range of from about 1 kHz to 25 kHz and (ii) a wavelength within the range of 200 nm to 5000 nm, wherein said laser light emerges from said distal end to generate an acoustic radiation field in a liquid ambient medium;
said laser light being coupled into said proximal ends at varying times, said laser light within individual strands of said bundle arriving at said distal ends at different times, wherein said different times are adjusted to control the directionality and shape of said acoustic radiation field, and wherein said different times are adjusted in combination with the different spatial positions of said individual strands.

24. A method for producing an acoustic radiation field through thermoelastic expansion of a liquid ambient medium located within vasculature, comprising:
inserting a fiber optic into said vasculature;
depositing laser energy in a volume of said liquid ambient medium comparable to the diameter of said fiber optic, in a time scale of duration less than the acoustic transit time across the length of said volume;
controlling said laser energy such that the maximum size of a cavitation bubble is approximately the same as the fiber diameter; and
pulsing said laser energy at a repetition rate such that multiple cycles of this process generates said acoustic radiation field in said liquid ambient medium.

25. The method of claim 21, further comprising synchronizing said repetition rate of said laser energy with the lifetime of said cavitation bubble to achieve resonant operation.

26. A method for producing an acoustic radiation field through vapor expansion of a liquid ambient medium located within vasculature, comprising:
inserting a fiber optic into said vasculature;
depositing laser energy in a small volume of said liquid ambient medium to produce a vapor bubble;
controlling said laser energy such that the maximum size of said vapor bubble is approximately the same as or less than the diameter of said vasculature; and
pulsing said laser energy at a repetition rate such that multiple cycles of the generation and collapse of said vapor bubble generates said acoustic radiation field in said liquid ambient medium.

27. The method of claim 26, further comprising the step of matching the pulse period of said laser energy to the lifetime of said vapor bubble to achieve resonant operation.

28. An apparatus, comprising:
a fiber optic for insertion into the vasculature to a point near an occlusion, wherein said fiber optic comprises a proximal end and a distal end; and
a laser to provide laser light for coupling into said proximal end, wherein said laser light has (i) a pulse frequency within the range of 10 Hz and 100 kHz, (ii) a wavelength within the range of 200 nm and 5000 nm and (iii) an energy density within the range of 0.01 J/cm$^2$ to 4 J/cm$^2$, wherein said laser light emerges from said distal end and generates an acoustic radiation field in a liquid ambient medium.

29. The apparatus of claim 28, wherein said laser light has a pulse frequency within the range of from about 1 kHz to 25 kHz.

30. The apparatus of claim 29, wherein said laser light has a pulse duration of less than 200 ns, wherein said acoustic radiation field is generated through thermoelastic expansion of said liquid ambient medium.

31. The apparatus of claim 29, wherein said acoustic radiation field is generated through superheated vapor expansion.

32. The apparatus of claim 29, wherein said acoustic radiation field is generated for the removal of said occlusion.

33. The apparatus of claim 32, wherein said occlusion is selected from a group consisting of atherosclerotic plaque and thrombus.

34. The apparatus of claim 29, further comprising a catheter and means for injecting said liquid ambient medium into the vasculature, wherein said fiber optic is located within said catheter, wherein a thrombolytic drug may be injected through said catheter into said liquid ambient medium to emulsify said occlusion.

35. The apparatus of claim 29, further comprising a catheter and means for injecting a radiographic contrast agent into the vasculature, wherein said fiber optic is located within said catheter, wherein a radiographic contrast agent may be injected through said catheter into said liquid ambient medium to facilitate visualization.

36. The apparatus of claim 29, further comprising feedback means for monitoring and controlling the magnitude of said acoustic radiation field induced in said liquid ambient medium.

37. The apparatus of claim 29, wherein said fiber optic comprises a tip having a shape that is selected from a group consisting of concave and planar.

38. The apparatus of claim 29, wherein said fiber optic comprises a variable diameter.

39. The apparatus of claim 29, wherein said fiber optic comprises a composite of glass and plastic.

40. The apparatus of claim 29, wherein the volume of said liquid ambient medium that is heated by said laser light is determined by the absorption depth of said laser light in said liquid ambient medium, and wherein said absorption depth is controlled to produce a desired thermoelastic stress in said volume.

41. The apparatus of claim 29, wherein said laser light has a pulse duration that is short enough to deposit substantially all of the laser energy into the absorbing fluid in a time scale shorter than the acoustic transit time across the smallest dimension of the absorbing region, wherein said acoustic radiation field is generated through thermoelastic expansion of said liquid ambient medium.

42. The apparatus of claim 29, wherein said fiber optic comprises a tip configured for use as an optical element to focus the light energy in said liquid ambient medium, wherein said tip is further configured to optimize the beam profile of said laser energy for generation of a desired acoustic radiation field.

43. The apparatus of claim 29, wherein said fiber optic comprises a tip having a surface that is prepared by a process selected from a group consisting of grinding, polishing and chemically etching.

44. The apparatus of claim 29, wherein said laser comprises means for changing the wavelength of said laser light produced by said laser.

45. The apparatus of claim 29, wherein said laser light has a pulse duration of less than 200 ns.

46. The apparatus of claim 29, wherein said liquid ambient medium is selected from a group consisting of blood, a biological saline solution, a biological saline solution containing an absorbing dye, a thrombolytic pharmaceutical, and thrombus.

47. The apparatus of claim 29, wherein said acoustic radiation field is generated through a mechanism selected from a group consisting of thermoelastic, thermodynamic, and a combination of thermoelastic and thermodynamic mechanisms, to remove said occlusion.

48. The apparatus of claim 28, wherein said liquid ambient medium is selected from a group consisting of blood, a biological saline solution, a biological saline solution containing an absorbing dye, a thrombolytic pharmaceutical, and thrombus.

49. The apparatus of claim 28, further comprising a catheter and means for injecting said liquid ambient medium into the vasculature, wherein said fiber optic is located within said catheter, wherein a thrombolytic drug may be injected through said catheter into said liquid ambient medium to emulsify said occlusion.

50. The apparatus of claim 49, further comprising a working channel that runs parallel to said fiber optic within said catheter, wherein said thrombolytic drug may be injected through said working channel to emulsify said occlusion.

51. The apparatus of claim 28, further comprising means for monitoring and controlling the magnitude of said acoustic radiation field induced in said liquid ambient medium.

52. The apparatus of claim 28, wherein said fiber optic comprises a tip having a shape that is selected from a group consisting of concave, and planar.

53. The apparatus of claim 28, wherein said fiber optic comprises a variable diameter.

54. The apparatus of claim 37, wherein said variable diameter fiber optic is tapered at the tip.

55. The apparatus of claim 28, wherein said fiber optic comprises a composite of glass and plastic.

56. The apparatus of claim 55, wherein said fiber optic composite of glass and plastic comprises a short section of plastic at the tip of said fiber optic, wherein said short section has a length within the range of 3 mm to 3 cm.

57. The apparatus of claim 28, wherein the volume of said liquid ambient medium that is heated by said laser light is determined by the absorption depth of said laser light in said liquid ambient medium, and wherein said absorption depth is controlled to produce a desired thermoelastic stress in said volume.

58. The apparatus of claim 28, wherein said laser light has a pulse duration that is short enough to deposit substantially all of the laser energy into the absorbing fluid in a time scale shorter thin the acoustic transit time across the smallest dimension of the absorbing region, wherein said acoustic radiation field is generated through thermoelastic expansion of said liquid ambient medium.

59. The apparatus of claim 25, wherein said fiber optic comprises a tip configured for use as an optical element to focus the light energy in said liquid ambient medium, wherein said tip is further configured to optimize the beam profile of said laser energy for generation of a desired acoustic radiation field.

60. The apparatus of claim 28, wherein said fiber optic comprises a tip having a surface that is prepared by a process selected from a group consisting of grinding, polishing and chemically etching.

61. The apparatus of claim 28, wherein said laser comprises means for changing the wavelength of said laser light produced by said laser.

62. The apparatus of claim 28, wherein said acoustic radiation field is generated through a mechanism selected from a group consisting of thermoelastic, thermodynamic, and a combination of thermoelastic and thermodynamic mechanisms, to remove said occlusion.

63. An apparatus, comprising:
  a fiber optic for insertion into the vasculature to a point near an occlusion, wherein said fiber optic comprises a proximal end and a distal end;
  a laser to provide laser light for coupling into said proximal end, wherein said laser light has (i) a pulse frequency within the range of 10 Hz and 100 kHz and (ii) a wavelength within the range of 200 nm and 5000 nm, wherein said laser light emerges from said distal end and generates an acoustic radiation field in a liquid ambient medium; and
  a catheter and means for injecting a radiographic contrast agent into the vasculature, wherein said fiber optic is located within said catheter, wherein said radiographic contrast agent may be injected through said catheter into said liquid ambient medium to facilitate visualization.

64. An apparatus for producing an acoustic radiation field through thermoelastic expansion of a liquid ambient medium located within vasculature, comprising:
  a fiber optic for insertion into said vasculature;
  means for depositing laser energy in a volume of said liquid ambient medium, wherein said volume is comparable to the diameter of said fiber optic, wherein said laser energy is deposited in a time scale of duration less than the acoustic transit time across the length of said volume;
  means for controlling said laser energy such that the maximum size of a cavitation bubble is approximately the same as the diameter of said fiber optic; and
  means for pulsing said laser energy at a repetition rate such that multiple cycles of this process generates said acoustic radiation field in said liquid ambient medium.

65. The apparatus of claim 64, further comprising means for synchronizing said repetition rate of said laser energy with the lifetime of said cavitation bubble.

66. An apparatus for producing an acoustic radiation field through vapor expansion of a liquid ambient medium located within vasculature, comprising:
  a fiber optic for insertion into said vasculature;
  means for depositing laser energy in a small volume of said liquid ambient medium to produce a vapor bubble;
  means for controlling said laser energy such that the maximum size of said vapor bubble is approximately the same as or less than the diameter of said vasculature; and
  means for pulsing said laser energy at a repetition rate such that multiple cycles of the generation and collapse of said vapor bubble generates said acoustic radiation field in said liquid ambient medium.

67. A method of removing an occlusion in a blood vessel, comprising:
  inserting a catheter into the vessel with an end adjacent the occlusion, the catheter including a plurality of optical fibers individually having a diameter of less than 400 microns and with ends thereof spatially distributed across the catheter end, and
  directing pulses of radiation within a wavelength range of from 200 to 5000 nanometers at a rate of more than 1 kiloHertz along individual ones of the fibers to exit their ends at different times and in a manner to generate acoustic vibrations within the vessel that emulsify the occlusion.

68. The method of claim 67, wherein the duration of individual ones of said radiation pulses is less than an acoustic transit time across a smallest dimension of a region within the vessel in which the radiation is absorbed.

69. The method of claim 68, wherein the smallest dimension of the absorption region is a dimension across an individual optical fiber.

70. The method of claim 67, wherein the duration of the individual radiation pulses is less than 20 nanoseconds.

71. The method of claim 67, wherein the rate of directing radiation pulses is within a range of 5 kiloHertz or more.

72. The method of claim 67, wherein the radiation emerging from the ends of the individual fiber optics has an energy density within a range of 0.01 to 4 Joules per square centimeter.

73. The method of claim 67, wherein the radiation pulses are directed in a manner to avoid directly abating the occlusion.

74. The method of claim 67, wherein the blood vessel in which the occlusion exists is within the cranial cavity of a human, said occlusion having caused an ischemic stroke.

75. The method of claim 74, wherein inserting the catheter includes inserting the end of the catheter into a vessel that is higher within the cranial cavity than the carotid artery.

76. The method of claim 67, additionally comprising delivering a stream of liquid into the vessel toward the occlusion.

77. The method of claim 76, wherein the delivered liquid includes thrombolytic drug.

78. The method of claim 76, wherein the delivered liquid includes a dye that absorbs said radiation.

79. The method of claim 76, wherein the delivered liquid includes a radiographic contrast agent, thereby to facilitate visualization.

80. The method of claim 67, wherein the occlusion that is removed includes a thrombus.

81. The method of claim 67, additionally comprising monitoring and controlling the acoustic vibrations as part of a feedback mechanism.

82. The method of claim 67, wherein the radiation pulses are directed in a manner to generate the acoustic vibrations within the vessel by creating a repetitively expanding and collapsing bubble in liquid within the vessel or in the occlusion.

83. The method of claim 82, wherein the bubbles are generated by vaporizing a volume of the liquid or the occlusion in which the radiation is absorbed.

84. The method of claim 67, wherein the radiation pulses are generated by a laser.

85. A method of removing a clot from a blood vessel within a human cranial cavity above the carotid artery, comprising:

inserting a catheter into the vessel with an end adjacent the clot, the catheter including a plurality of optical fibers individually having a diameter of less than 400 microns and with ends thereof spatially distributed across the catheter end, introducing a stream through a lumen of the catheter that is directed toward the clot, and directing pulses of radiation within a wavelength range of from 200 to 5000 nanometers along individual ones of the fibers at different times with a rate of more than 1 kiloHertz, said radiation pulses exiting the fiber ends to be absorbed within a region of liquid in the vessel or the clot in a manner to generate acoustic vibrations therein that emulsify the clot, wherein the duration of individual ones of said radiation pulses is less than an acoustic transit time across a smallest dimension of said absorption region.

86. The method according to claim 85, wherein the smallest dimension of the absorption region is a dimension across an individual optical fiber.

87. The method of claim 85, wherein the duration of the individual radiation pulses is less than 20 nanoseconds.

88. The method of claim 85, wherein the rate of directing radiation pulses is within a range of 5 kiloHertz or more.

89. The method of claim 85, wherein the radiation emerging from the ends of the individual fiber optics has an energy density within a range of 0.01 to 4 Joules per square centimeter.

90. The method of claim 85, wherein the radiation pulses are directed in a manner to avoid directly abating the clot.

91. The method of claim 85, wherein the delivered liquid includes thrombolytic drug.

92. The method of claim 85, wherein the delivered liquid includes a dye that absorbs said radiation.

93. The method of claim 85, wherein the delivered liquid includes a radiographic contrast agent, thereby to facilitate visualization.

94. The method of claim 85, additionally comprising monitoring and controlling the acoustic vibrations as part of a feedback mechanism.

95. The method of claim 85, wherein the radiation pulses are directed in a manner to generate the acoustic vibrations within the vessel by creating a repetitively expanding and collapsing bubble in liquid within the vessel or the clot.

96. The method of claim 85, wherein the bubbles are generated by vaporizing said absorption region.

97. A system for opening an occlusion within a blood vessel by generating acoustical vibrations within the vessel, comprising:

a flexible catheter adapted to be inserted into said vessel and including a plurality of optical fibers individually having a diameter of less than 400 microns and with first ends thereof spatially distributed across a free end of the catheter, a source of radiation pulses within a wavelength range of from 200 to 5000 nanometers optically coupled with second ends of said optical fibers in a manner to provide said radiation pulses along individual ones of the fibers to exit their first ends at different times with a repetition rate of more than 1 kiloHertz, a fluid channel terminating at the free end of the catheter for carrying liquid into the vessel during application of radiation pulses, and a feedback mechanism that monitors and controls acoustic vibrations generated within the vessel by the radiation pulses.

98. The system according to claim 97, wherein the radiation source provides individual pulses with a duration of less than 20 nanoseconds.

99. The system according to claim 97, wherein the radiation source provides the pulses with a repetition rate of 5 kiloHertz or more.

100. The system according to claim 97, wherein the catheter has an outside diameter at its said free end of less than 2.5 millimeters.

101. An apparatus for opening an occlusion within a fluid-containing body vessel by generating acoustical vibrations within the vessel, comprising:

a flexible catheter adapted to be inserted into said vessel and including a plurality of optical fibers individually having a diameter of less than 400 microns and with first ends thereof spatially distributed across a free end of the catheter, and a source of radiation pulses within a wavelength range of from 200 to 5000 nanometers optically coupled with second ends of said optical fibers in a manner to provide said radiation pulses along individual ones of the fibers to exit their first ends at different times with a repetition rate of more than 1 kiloHertz, such that said pulses of radiation are absorbed by the vessel fluid or the occlusion in a manner to generate said acoustical vibrations that emulsify said occlusion.

102. The apparatus of claim 101, further comprising a fluid channel terminating at the free end of the catheter for carrying liquid into the vessel during application of said radiation pulses.

103. The apparatus of claim 102, wherein said liquid includes one or more of a thrombolytic drug, a dye that absorbs said radiation, and a radiographic contrast agent to facilitate visualization.

104. The apparatus of claim 101, wherein the duration of individual ones of said radiation pulses is less than an acoustic transit time across a smallest dimension of a region within the vessel in which the radiation is absorbed.

105. The apparatus of claim 104, wherein the smallest dimension of the absorption region is a dimension across an individual optical fiber.

106. The apparatus of claim 101, wherein the duration of the individual radiation pulses is less than 20 nanoseconds.

107. The apparatus of claim 101, wherein the rate of directing radiation pulses is within a range of 5 kiloHertz or more.

108. The apparatus of claim 101, wherein the radiation emerging from the ends of the individual fiber optics has an energy density within a range of 0.01 to 4 Joules per square centimeter.

109. The apparatus of claim 101, wherein the radiation pulses are directed in a manner to avoid directly abating the occlusion.

110. The apparatus of claim 101, wherein the body vessel in which the occlusion exists is within the carotid artery or the cranial cavity of a human.

111. The apparatus of claim 110, wherein said occlusion caused an ischemic stroke.

112. The apparatus of claim 101, wherein the occlusion that is opened includes a thrombus.

113. The apparatus of claim 112, wherein the bubbles are generated at least in part by vaporizing a volume of the vessel fluid or the occlusion in which the radiation is absorbed.

114. The apparatus of claim 101, wherein the said acoustical vibrations are generated by creating a repetitively expanding and collapsing bubble in fluid within the vessel fluid or in the occlusion.

115. The apparatus of claim 101, wherein the radiation pulses are generated by a laser.

116. The apparatus of claim 101, wherein the catheter has an outside diameter at its said free end of less than 2.5 millimeters.

117. An apparatus for opening a clot within a blood vessel in a human cranial cavity by generating acoustical vibrations within the vessel, comprising:

a flexible catheter adapted to be inserted into said vessel and including a plurality of optical fibers individually having a diameter of less than 400 microns and with first ends thereof spatially distributed across a free end of the catheter, and a source of radiation pulses within a wavelength range of from 200 to 5000 nanometers optically coupled with second ends of said optical fibers in a manner to provide said radiation pulses along individual ones of the fibers to exit their first ends at different times with a repetition rate of more than 1 kiloHertz, wherein the duration of individual ones of said radiation pulses is less than an acoustic transit time across a smallest dimension of a region within the vessel in which the radiation is absorbed, such that said pulses of radiation generate said acoustical vibrations which emulsify at least a portion of said occlusion without directly abating said occlusion.

\* \* \* \* \*